United States Patent
Schwan

[11] 3,993,617
[45] Nov. 23, 1976

[54] ANTIFUNGAL 2-SUBSTITUTED PHTHALIMIDINES

[75] Inventor: Thomas James Schwan, Norwich, N.Y.

[73] Assignee: Morton-Norwich Products, Inc., Norwich, N.Y.

[22] Filed: Oct. 30, 1975

[21] Appl. No.: 627,229

[52] U.S. Cl............................. 260/325 PH; 424/274
[51] Int. Cl.$^2$........................................ C07D 209/46
[58] Field of Search............................... 260/325 PH

[56] References Cited
UNITED STATES PATENTS
3,317,558   5/1967   Becke et al.................. 260/325 PH Primary Examiner—Elbert L. Roberts
Assistant Examiner—S. P. Williams
Attorney, Agent, or Firm—Anthony J. Franze

[57] ABSTRACT

Certain 2-substituted phthalimidines of the formula:

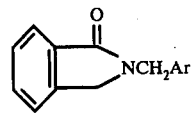

wherein Ar is 3,4-dichlorophenyl and 2-naphthyl possess activity as antifungal agents.

3 Claims, No Drawings

ANTIFUNGAL 2-SUBSTITUTED PHTHALIMIDINES

This invention relates to chemical compounds. In particular it is concerned with compounds of the formula:

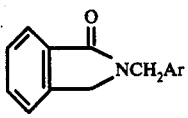

wherein Ar is 3,4-dichlorophenyl and 2-naphthyl. These compounds are antifungal agents. At concentrations of 100μg/ml in Sabouraud's dextrose broth they inhibit the growth of *Microsporum canis* in the commonly employed agar diffusion test. They are adapted to be combined in various forms such as elixirs, dusts, unguents, solutions and suspensions to provide compositions inimical to fungal growth.

The preparation of the compounds of this invention can be accomplished according to the following scheme:

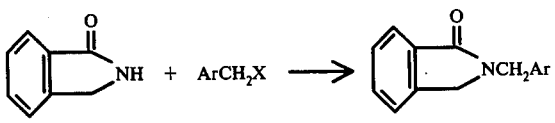

wherein Ar has the significance previously ascribed and X is halogen. The reaction is conducted in the presence of a base such as sodium hydride. A solvent inert under the conditions of the reaction such as toluene is employed.

In order that this invention may be readily available to and understood by those skilled in the art the following examples are appended:

EXAMPLE I

N-(3,4-Dichlorobenzyl)phthalimidine

A mixture of 13.3 g (0.10 mole) of phthalimidine, 8.0 g sodium hydride-60% in mineral oil (4.80 g, 0.20 mole), and 19.5 g (0.10 mole) 3,4-dichlorobenzyl chloride in 175 ml toluene was stirred and refluxed for 18 hours. Methanol (25 ml) was added to destroy excess sodium hydride and the mixture was concentrated to dryness in vacuo. The residue was partitioned between 200 ml water and 200 ml chloroform. The chloroform layer was separated and the aqueous layer was extracted with 2 x 100 ml chloroform. The combined extracts were washed with 200 ml water, dried (magnesium sulfate), and concentrated to dryness in vacuo to give 33.5 g of an oil that was washed with 75 ml cold hexane.

Crystallization from 125 ml toluene gave 13.1 g of material which was boiled with 325 ml heptane. The heptane solution was combined with the toluene filtrate above and the mixture was concentrated to dryness. Crystallization of the residue from 30 ml toluene gave 5.1 g (17%) of the product, m.p. 92°–105°. Further recrystallization from heptane gave the analytical sample, m.p. 105°–106°.

Anal. Calcd. for $C_{15}H_{11}Cl_2NO$: C, 61.66; H, 3.80, N, 4.80.

Found: C, 61.71; H, 3.92, N, 4.70.

EXAMPLE II

N-(2-Naphthylmethyl)phthalimidine

A mixture of phthalimidine (16.1 g, 0.121 mole), 30.94 g, (0.14 mole) 2-bromomethyl)naphthalene), and 8.0 g sodium hydride-60% in mineral oil (i.e. 4.80 g, 0.20 mole) in 150 ml toluene was stirred and refluxed for 16 hours, cooled, and 3.0 ml methanol was added. After dilution with 250 ml water the mixture was stirred for 1 hour. The toluene layer was separated and the aqueous layer was extracted with 100 ml water, dried (magnesium sulfate), and concentrated to dryness in vacuo. Crystalization from 50 ml toluene gave 12.6 g (46%) of the product, m.p. 97°–102°. Further recrystallization from toluene gave the analytical sample, m.p. 103°–106°.

Anal. Calcd. for $C_{19}H_{15}NO$: C, 83.49; H, 5.53.
Found: C, 83.66, H, 5.63.

What is claimed is:
1. A compound of the formula:

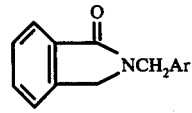

wherein Ar is 3,4-dichlorophenyl or 2-naphthyl.
2. The compound N-(3,4-dichlorobenzyl)phthalimidine.
3. The compound N-(2-naphthylmethyl)phthalimidine.

* * * * *